[US010213208B2](#)

(12) United States Patent
Massicotte

(10) Patent No.: US 10,213,208 B2
(45) Date of Patent: Feb. 26, 2019

(54) TOROIDAL BALLOON FOR EXTERNAL OR INTERNAL COMPRESSION WITH UNIQUE INSERTION OR REMOVAL

(71) Applicant: J. Mathieu Massicotte, North Reading, MA (US)

(72) Inventor: J. Mathieu Massicotte, North Reading, MA (US)

( * ) Notice: Subject to any disclaimer, the term of this patent is extended or adjusted under 35 U.S.C. 154(b) by 590 days.

(21) Appl. No.: 14/665,491

(22) Filed: Mar. 23, 2015

(65) Prior Publication Data

US 2015/0320982 A1 Nov. 12, 2015

Related U.S. Application Data

(60) Provisional application No. 61/969,416, filed on Mar. 24, 2014.

(51) Int. Cl.
*A61M 25/10* (2013.01)
*A61M 25/00* (2006.01)
(Continued)

(52) U.S. Cl.
CPC .... *A61B 17/12136* (2013.01); *A61B 17/1204* (2013.01); *A61B 17/12036* (2013.01); *A61B 17/12104* (2013.01); *A61B 17/135* (2013.01); *A61F 2/0013* (2013.01); *A61F 5/08* (2013.01); *A61M 16/0666* (2013.01); *A61M 25/0017* (2013.01); *A61M 25/1002* (2013.01); *A61M 25/10181* (2013.11); *A61B 17/24* (2013.01); *A61B 2017/00557* (2013.01); *A61F 2230/0065* (2013.01); *A61M 25/1011* (2013.01);
(Continued)

(58) Field of Classification Search
CPC .......... A61B 17/12036; A61B 17/1204; A61B 17/12104; A61B 17/12136; A61B 17/135; A61B 17/24; A61B 2017/00557; A61B 2017/3435; A61F 2/0013; A61F 2230/0065; A61F 5/08; A61M 16/0666; A61M 2025/0687; A61M 2025/1031; A61M 2025/105; A61M 2025/1075; A61M 2025/1093; A61M 2210/0618; A61M 25/0017; A61M 25/1002; A61M 25/1011; A61M 25/10181; A61M 29/02
See application file for complete search history.

(56) References Cited

U.S. PATENT DOCUMENTS 3,669,099 A * 6/1972 Silverman .............. A61B 10/02
156/287
4,820,270 A * 4/1989 Hardcastle .............. A61L 29/06
264/167

(Continued)

*Primary Examiner* — Adam Marcetich
(74) *Attorney, Agent, or Firm* — Gesmer Updegrove LLP

(57) ABSTRACT

A balloon is fashioned in the shape of a modified toroid that changes position by rotation. As a result, the toroidal balloon is an improvement over existing balloons for dilation and applying pressure since it can apply the pressure to both the external surface and the surface lining the balloon's internal channel and change position while applying that pressure. In addition, the toroidal balloon can apply a biologically active substance or medical device to a biological wall then leave that substance or device in place with the rotational extraction of the balloon. Other balloons for dilation or application of a substance or device need to be deflated to change their position.

8 Claims, 12 Drawing Sheets

(51) Int. Cl.
*A61B 17/12* (2006.01)
*A61F 5/08* (2006.01)
*A61M 16/06* (2006.01)
*A61F 2/00* (2006.01)
*A61B 17/135* (2006.01)
*A61B 17/24* (2006.01)
*A61B 17/00* (2006.01)
*A61M 29/02* (2006.01)

(52) U.S. Cl.
CPC ....... *A61M 29/02* (2013.01); *A61M 2025/105* (2013.01); *A61M 2025/1093* (2013.01); *A61M 2210/0618* (2013.01)

(56) References Cited

U.S. PATENT DOCUMENTS

| | | | |
|---|---|---|---|
| 4,875,480 A * | 10/1989 | Imbert | A61F 2/958 606/194 |
| 5,195,970 A | 3/1993 | Gahara | |
| 5,364,345 A * | 11/1994 | Lowery | A61M 25/0119 600/116 |
| 5,458,573 A * | 10/1995 | Summers | A61M 25/0119 604/101.04 |
| 5,632,761 A | 5/1997 | Smith et al. | |
| 5,902,286 A * | 5/1999 | Reitz | A61M 25/0119 604/264 |
| 6,264,633 B1 * | 7/2001 | Knorig | A61M 25/10 128/898 |
| 8,343,170 B2 | 1/2013 | Massicotte | |
| 8,529,581 B2 | 9/2013 | Massicotte | |
| 2001/0023332 A1 | 9/2001 | Hahnen | |
| 2002/0013542 A1 * | 1/2002 | Bonadio | A61B 17/3423 601/134 |
| 2002/0045906 A1 * | 4/2002 | Kelly | A61B 1/00151 606/108 |
| 2003/0153875 A1 * | 8/2003 | Ostfeld | A61M 25/0017 604/171 |
| 2004/0243144 A1 * | 12/2004 | Bonadio | A61B 1/00151 606/108 |
| 2006/0020164 A1 * | 1/2006 | Butler | A61B 1/00151 600/115 |
| 2007/0038227 A1 * | 2/2007 | Massicotte | A61B 17/22032 606/127 |
| 2007/0213661 A1 * | 9/2007 | Gobel | A61F 2/0013 604/96.01 |
| 2008/0051706 A1 * | 2/2008 | Hirszowicz | A61B 17/22032 604/103.03 |
| 2008/0086083 A1 | 4/2008 | Towler | |
| 2008/0171991 A1 * | 7/2008 | Kourakis | A61M 25/0119 604/175 |
| 2008/0215031 A1 * | 9/2008 | Belfort | A61B 17/12099 604/500 |
| 2009/0270964 A1 | 10/2009 | Huetter et al. | |
| 2010/0023106 A1 * | 1/2010 | Meyer | A61B 17/12136 623/1.11 |
| 2010/0191183 A1 * | 7/2010 | Tanghoej | A61M 25/0017 604/96.01 |
| 2011/0028943 A1 * | 2/2011 | Lawson | A61M 25/0017 604/544 |
| 2013/0116559 A1 * | 5/2013 | Levin | A61M 3/0279 600/437 |
| 2013/0331824 A1 * | 12/2013 | Kim | A61M 25/0017 604/544 |

* cited by examiner

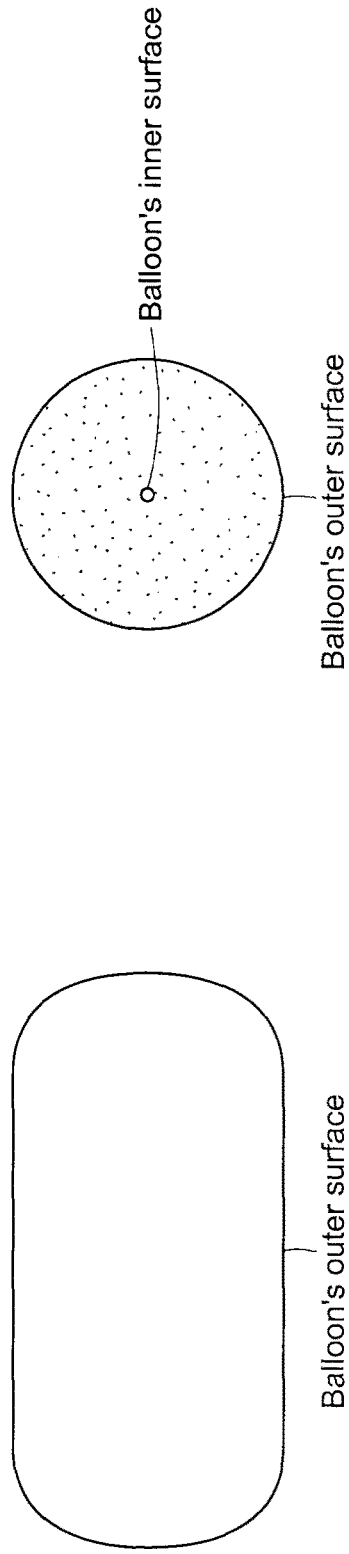
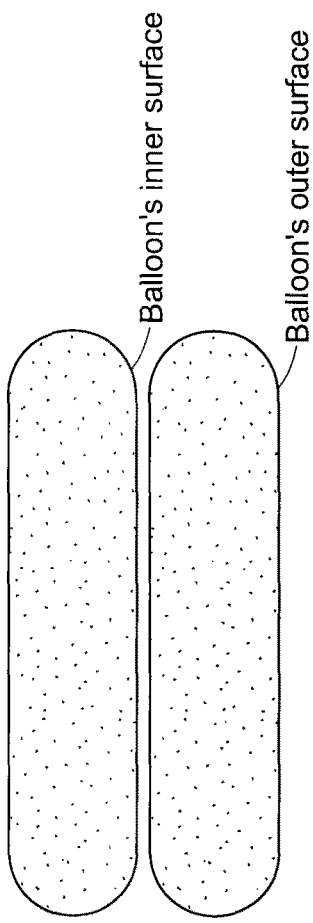

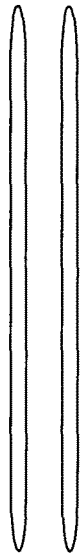
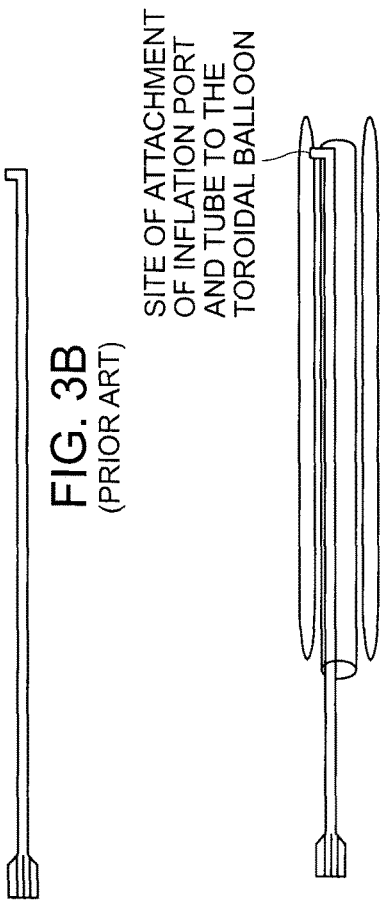
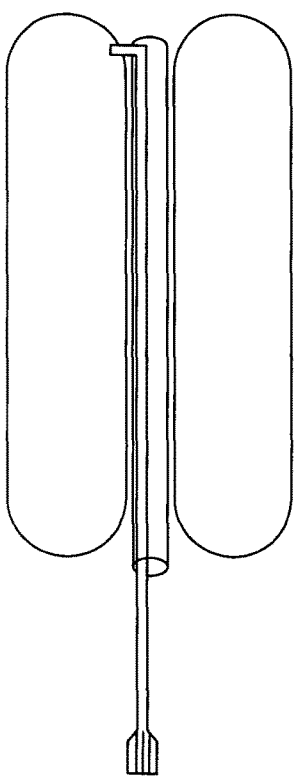
FIG. 3A (PRIOR ART)
FIG. 3B (PRIOR ART)
FIG. 3C (PRIOR ART)
FIG. 3D (PRIOR ART)
FIG. 3E (PRIOR ART)
FIG. 3F (PRIOR ART)
SITE OF ATTACHMENT OF INFLATION PORT AND TUBE TO THE TOROIDAL BALLOON

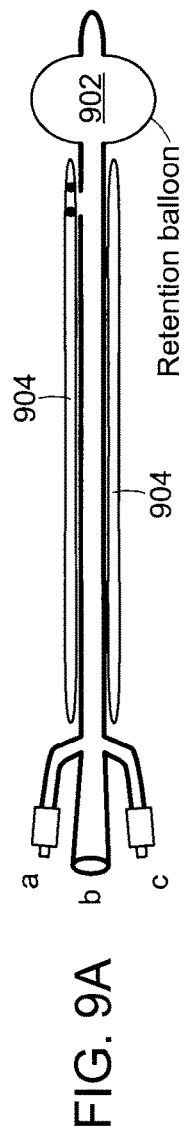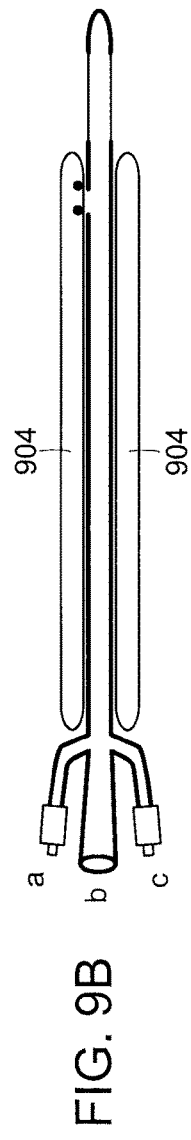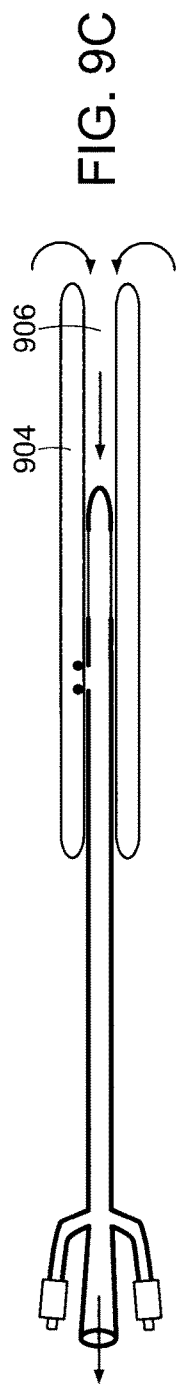

TOROIDAL BALLOON FOR EXTERNAL OR INTERNAL COMPRESSION WITH UNIQUE INSERTION OR REMOVAL

PRIORITY

The present invention claims priority to U.S. Provisional Application Ser. No. 61/969,416 filed on Mar. 24, 2014, the entire contents are incorporated herein by reference in its entirety.

BACKGROUND OF THE INVENTION

Field of Invention

The present invention relates generally to medical devices. More specifically, the present invention involves a specially designed toroidal balloon that can be rolled into a place of function or away from its place of function (e.g., after use) without injuring the adjacent tissue, where the toroidal balloon is used to apply a pressure across its external surface or the surface surrounding its inner channel.

Discussion of Prior Art

Existing balloons used commonly in the medical field are designed for dilation, creation of a space, securing a device in place or application of a medical device. They are spherical or sausage-shaped when inflated. Such fixed shapes are static by nature and limit the balloon's application and utility. An example of a sausage-shaped balloon is one to dilate a ureter for insertion of a scope or removal of a urinary stone. Another example is a balloon used to dilate a stenosis involving a coronary artery and to place a coronary artery stent. In general, in such prior art systems, these balloons must be deflated during insertion and withdrawal.

Toroidal balloons have properties that have improved function, safety and utility over existing balloons. Toroidal balloons are donut-shaped and, like a ring, have an outer surface and an inner surface that surrounds the inner channel. Because of its inner channel, toroidal balloons have benefits over simple balloons. There are many examples of toroidal balloons in the prior art, wherein such toroidal balloons are generally used to dilate or to form a seal between an artificial tube and a hollow structure, as in the case of the inflatable cuff on an endotracheal tube.

The U.S. patent to Gahara (U.S. Pat. No. 5,195,970) discloses a Collapsible Balloon Catheter. The disclosed balloons and balloon catheters are used in medical dilatation procedures with particular emphasis being placed on the ability of such devices to withstand significant inflation pressures and also address problems associated with "winging" during deflation. While the disclosed balloon is used for dilation, it is static and not moveable.

The U.S. patent to Smith et al. (U.S. Pat. No. 5,632,761) discloses Inflatable Devices for Separating Layers of Tissue, and Methods of Using. The disclosed apparatus relates to inflatable tissue separation devices that are static and not moveable.

The U.S. patent application to Hahnen (US 2001/0023332 A1) discloses an Inflatable Cannula and Method of Using Same. Disclosed with in a cannula or catheter that can be introduced to a small port and be inflated to accommodate a large flow of fluids, or can serve as a conduit or port to apply other medical therapy, such as surgical instruments, dilatation catheters, atherectomy devices, filters, aspirators, and pressure monitors. In this setup, the toroidal balloon may be constructed over a catheter or tube. However, the inflatable cannula is static and not moveable.

The U.S. Patent Publication to Towler (US 2008/0086083 A1) discloses Inflatable Toroidal-Shaped Balloons. The disclosed toroidal balloon is provided with a central opening traversing the balloon in an inflated state, where the balloon is useful to achieve larger outer diameters than conventional balloons. However, as in the previous piece of prior art, the inflated balloons are static with no movement.

The U.S. Patent Publication to Huetter et al. (US 2009/0270964 A1) discloses a "Toroidal Balloon System and Method of Use." The disclosed toroidal balloon comprises an inflatable cylinder, which compresses an outside wall and maintains a passage within it. It is important to note that, when inflated, the cylinder is static and has no capability of moving.

While the prior art above describes a toroidal balloon, such balloons are more of a donut-shape than an elongated-donut-shape, as described in this disclosure. Further, the prior art also fail to disclose any rotational movement of the toroidal balloon as described in this disclosure.

However, absent in all references described above is a toroidal balloon which, in addition to being movable, is also used for the express purpose of applying pressure along its outside or inner wall. Furthermore, also absent in such prior art is an inflatable toroidal balloon which, under pressure, allows not only the application of a biologically active substance or medical device to a biological surface adjacent to the toroidal balloon's external or internal surface, but also the option to leave the substance or device in place against the biological wall with the rotational removal of the toroidal balloon.

Whatever the precise merits, features, and advantages of the above cited references, none of them achieve or fulfill the purposes of the present invention.

SUMMARY OF THE INVENTION

In one embodiment, the present invention provides a nasal splint comprising: (A) a first tube and a first toroidal balloon constructed over at least a portion of the first tube, a first internal balloon surface of the first toroidal balloon contacting outside of the first tube and a first external balloon surface of the first toroidal balloon contacting tissue in a first nasal cavity to the left of a nasal septum, the first toroidal balloon deployed in the first nasal cavity in a deflated or partially inflated state; (B) a second tube and a second toroidal balloon constructed over at least a portion of the second tube, a second internal balloon surface of the second toroidal balloon contacting outside of the second tube and a second external balloon surface of the second toroidal balloon contacting tissue in a second nasal cavity to the right of the nasal septum, the second toroidal balloon deployed in the second nasal cavity in a deflated or partially inflated state; and (C) a pressure means to inflate the first and second toroidal balloon to apply a predetermined amount of pressure (picked, for example, to avoid pressure points and local ischemia) in the left and right nasal cavities. In an extended embodiment, upon completion of a procedure associated with the nasal splint, the pressure means deflates the first and second toroidal balloon, where the first and second toroidal balloon are each removed via an inversion of their corresponding internal balloon surface and external balloon surface, with such inversion allowing low friction extraction of the first and second toroidal balloons without sliding of the external balloon surfaces against wall tissue in the first and second nasal cavities. In an extended embodiment, the first and second toroidal balloons are in the partially inflated state when deployed in the first and second nasal cavities, respectively, with the deployment being done via an inversion of their corresponding internal balloon surface and external balloon surface, with such inversion allowing low friction placement of the first and second toroidal balloons in the first and second nasal cavities without sliding of the external balloon surfaces against wall tissue in the first and second nasal cavities.

In another embodiment, the present invention provides a tamponade device for epistaxis comprising: (A) a tube and a toroidal balloon constructed over at least a portion of the tube, an internal balloon surface of the toroidal balloon contacting outside of the tube and an external balloon surface of the toroidal balloon contacting tissue in a nasal cavity which is the site of the epistaxis, the toroidal balloon deployed in the nasal cavity in a deflated or partially inflated state; and (B) a pressure means to inflate the toroidal balloon to apply a predetermined amount of pressure (picked, for example, to avoid pressure points and local ischemia) to the site of epistaxis. In an extended embodiment, upon completion of a procedure associated with the tamponade device (e.g., successful clotting at the site of epistaxis), the pressure means deflates the toroidal balloon, with the toroidal balloon removed via an inversion of its internal balloon surface and external balloon surface, with such inversion allowing low friction extraction of the toroidal balloon without sliding of the external balloon surfaces against wall tissue in the site of epistaxis. In an extended embodiment, the toroidal balloon is in the partially inflated state when deployed in the site of epistaxis, and the deployment done via an inversion of the internal balloon surface and the external balloon surface, with such inversion allowing low friction placement of the toroidal balloon in the site of epistaxis without sliding of the external balloon surfaces against wall tissue in the site of epistaxis. In an extended embodiment, the internal and external balloon surfaces are coated with a coagulogenic substance. Non-limiting examples of such coagulogenic substances include Surgicel® hemostat, Gelfoam® or other hemostatic agent that may be applied to the biological surface upon inflation of the toroidal balloon and, subsequently, left in place with the rotational removal of the toroidal balloon.

In another embodiment, the present invention provides a urethral catheter comprising: (A) a tube having a retention balloon at distal end; (B) a toroidal balloon constructed over a portion of the tube, an internal balloon surface of the toroidal balloon contacting outside of the tube and an external balloon surface of the toroidal balloon contacting a urethral wall, the toroidal balloon deployed in the urethra in a deflated or partially inflated state and not covering the retention balloon; and (C) a first pressure means to inflate the retention balloon when deployed in the urethra and deflate the same when a urethral procedure is complete; (D) a second pressure means to inflate the toroidal balloon, with the deflated retention balloon extracted via an inversion of the toroidal balloon's internal balloon surface and external balloon surface, with such inversion allowing low friction extraction of the retention balloon without sliding of the external balloon surfaces against the urethral wall. In an extended embodiment, the toroidal balloon is at least in a partially inflated state when deployed in the urethra, and the retention balloon is deployed in a deflated state in the urethra via an inversion of the toroidal balloon's internal balloon surface and external balloon surface, with such inversion allowing low friction placement of the retention balloon without sliding of the external balloon surfaces against the urethral wall. In an extended embodiment, the external and/or internal balloon surfaces are coated with a biologically active substance such as a coagulogenic or an antimicrobial agent. In an extended embodiment, the first and second pressure means are the same. For example, the same syringe to inflate the retention balloon may be used also to inflate the toroidal balloon.

In another embodiment, the present invention provides a urethral catheter for tamponade of urethral bleeding comprising: (a) a tube having a retention balloon at distal end; (b) a toroidal balloon constructed over a portion of the tube, an internal balloon surface of the toroidal balloon contacting outside of the tube and an external balloon surface of the toroidal balloon contacting a urethral wall, the toroidal balloon deployed in the urethra in a deflated or partially inflated state and not covering the retention balloon, the internal and external balloon surfaces coated with a coagulogenic substance; (c) a first pressure means to inflate the retention balloon when (the more proximal) toroidal balloon is aligned at the site of urethral bleeding in the urethra and the pressure means is used to deflate the retention balloon when a urethral procedure is complete; and (d) a second pressure means to inflate the toroidal balloon when deployed in the site of urethral bleeding, where the inflated toroidal balloon provides tamponade and/or is coated with the coagulogenic substance (such as, but not limited to, Surgicel® hemostat, Gelfoam® or other hemostatic agent) and contacts a urethral wall that is the site of urethral bleeding. In an extended embodiment, where, when the urethral bleeding is contained, the partially deflated retention balloon extracted via an inversion of the toroidal balloon's internal balloon surface and external balloon surface, with such inversion allowing low friction extraction of the retention balloon without sliding of the external balloon surfaces against the urethral wall leaving behind the hemostatic agent that was applied to the urethral wall. In an extended embodiment, the toroidal balloon is in a partially inflated state when deployed in the urethra, and the retention balloon is deployed in a deflated state in the urethra via an inversion of the toroidal balloon's internal balloon surface and external balloon surface, with such inversion allowing low friction placement of the retention balloon without sliding of the external balloon surfaces against the urethral wall. In an extended embodiment, the first and second pressure means are the same. For example, the same syringe to inflate the retention balloon may be used also to inflate the toroidal balloon.

In another embodiment, the present invention provides a device for treating urinary incontinence comprising: an inflated toroidal balloon having internal and external balloon surfaces and a diaphragm held in place in a channel formed between opposing internal balloon surfaces, where deployment over a penis is done via an inversion of the internal and external balloon surfaces, with such inversion allowing low friction placement of the toroidal balloon over the penis and such inversion maintaining the diaphragm within the channel, where the pressure exerted by the toroidal balloon on the penis is enough to disallow passage of urine through the urethra while allowing blood flow to the tissues.

In another embodiment, the present invention provides a tourniquet comprising: an inflated toroidal balloon having internal and external balloon surfaces, where deployment over a region proximate to a bleeding wound is done via an inversion of the internal and external balloon surfaces, with such inversion allowing low friction placement of the toroidal balloon in the region proximate to the bleeding wound, where the pressure exerted by the toroidal balloon in the region proximate to the bleeding wound is enough to prevent blood flow to the wound.

BRIEF DESCRIPTION OF THE DRAWINGS

FIGS. 1A-1C depict simple diagrams of a toroidal balloon. FIG. 1A is an external view. The balloon is hot dog shaped although it contains an inner channel that is not visible from the outside. FIG. 1B is a two-dimensional view of the toroidal balloon in transverse section. FIG. 1C is a two dimensional view in coronal section.

FIGS. 3A-3F depict a collection of diagrams to describe the components of a toroidal balloon device. FIG. 3A depicts a generic tube. FIG. 3B depicts a tube for inflation of the balloon. FIG. 3C depicts a deflated balloon. FIG. 3D depicts an inflated balloon. FIG. 3E depicts a deflated toroidal balloon device constructed over a tube. FIG. 3F depicts an inflated toroidal balloon device over a tube.

In FIG. 5A, the tube is located within the toroidal balloon, just prior to being withdrawn. In FIG. 5B, the tube is withdrawn which causes rotation of the toroidal balloon. In FIG. 5C, the tube is used to either retract or advance the toroidal balloon.

FIG. 7A shows the inflated balloon in a two dimensional para-sagital section. FIG. 7B shows the inflated balloon in two-dimensional coronal section at the level of the eyes.

FIGS. 9A-9C depict an example of a toroidal balloon constructed over a urethral catheter where both tube and inflation port are attached at the same site on the toroidal balloon. In FIG. 9A, Port "a" inflates or deflates the toroidal balloon, port "c" inflates or deflates the retention balloon, where the urinary drainage channel drains at "b." In FIG. 9B, before removal of the catheter, the retention balloon is deflated and the toroidal balloon is inflated. In FIG. 9C, the catheter is withdrawn without friction and the outside wall is not drawn against the urethra.

DESCRIPTION OF THE PREFERRED EMBODIMENTS

Figure 2:
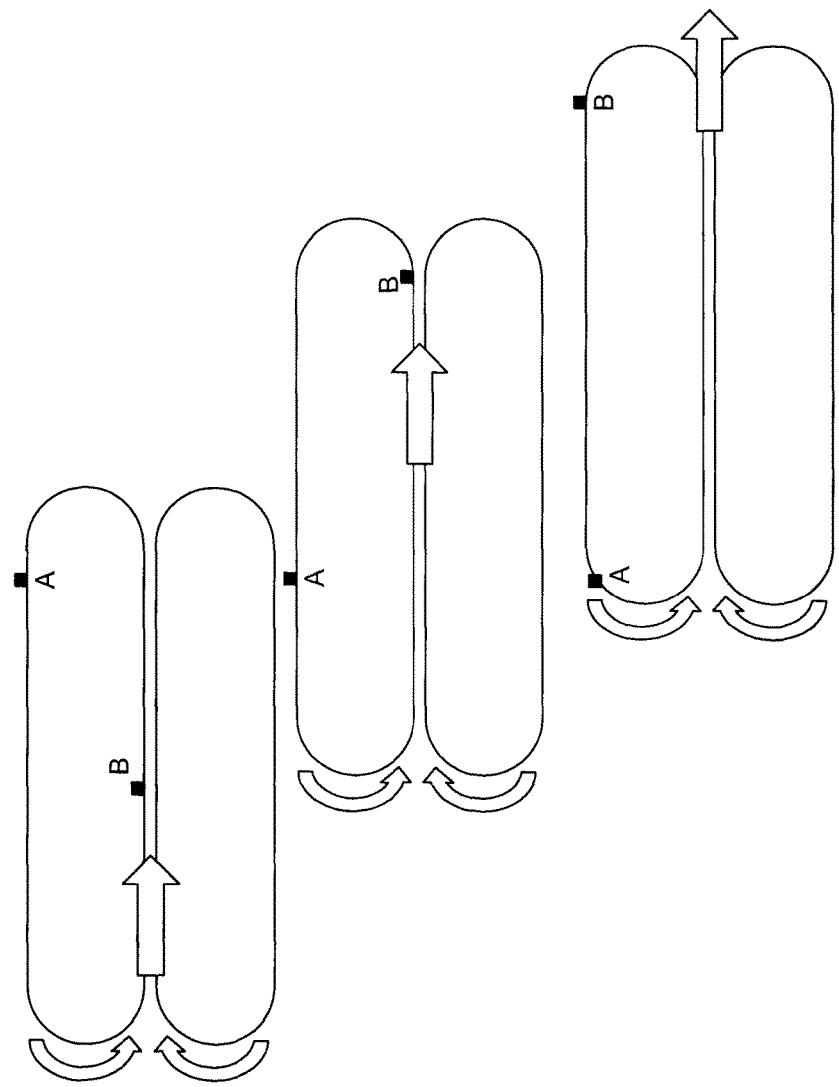
FIG. 2 depicts a diagram of toroidal balloon rotation in 2-Dimension Coronal Section, where points A and B are fixed reference points on the balloon's wall.

While this invention is illustrated and described in a preferred embodiment, the device may be produced in many different configurations, forms and materials. There is depicted in the drawings, and will herein be described in detail, a preferred embodiment of the invention, with the understanding that the present disclosure is to be considered as an exemplification of the principles of the invention and the functional specifications for its construction and is not intended to limit the invention to the embodiment illustrated. Those skilled in art will envision many other possible variations within the scope of the present invention.

Applicant notes the following two US patents by Massicotte et al. (with one common inventor): (1) U.S. Pat. Nos. 8,529,581, and (2) 8,343,170, both of which describe devices that function, in part, based on the rotation of the toroidal balloon. However, as with the prior art, absent in these references is a toroidal balloon which, in addition to being movable, is also used for the express purpose of applying pressure along its outside or inner wall.

FIGS. 1A-1B depict a toroidal balloon. Particularly, FIG. 1A depicts an outside view showing the external appearance of a toroidal balloon. It has roughly the same external appearance of a simple sausage-shaped balloon. FIG. 1B depicts a transverse section of the toroidal balloon shown in FIG. 1A. FIG. 1C depicts a coronal section of the toroidal balloon in FIG. 1A.

One key differentiating factor of the toroidal balloon in this invention is its ability to rotate along its internal or external surface, depending upon its construction and its function. FIG. 2 is a two dimensional diagram showing the rotation of a toroidal balloon. The benefit of a balloon with toroidal rotation is that when the inflated balloon is moved, the outside walls (or inside walls depending upon the function of the balloon) of the balloon are not dragged across the opposing biological wall which can result for example in injury to the biological wall and unnecessary pain. With movement of a toroidal balloon, the walls of the balloon are "lifted" perpendicularly from the opposing internal or external surface without dragging of the balloon surface against the surface avoiding pain and trauma to the biological surface.

Figure 4:
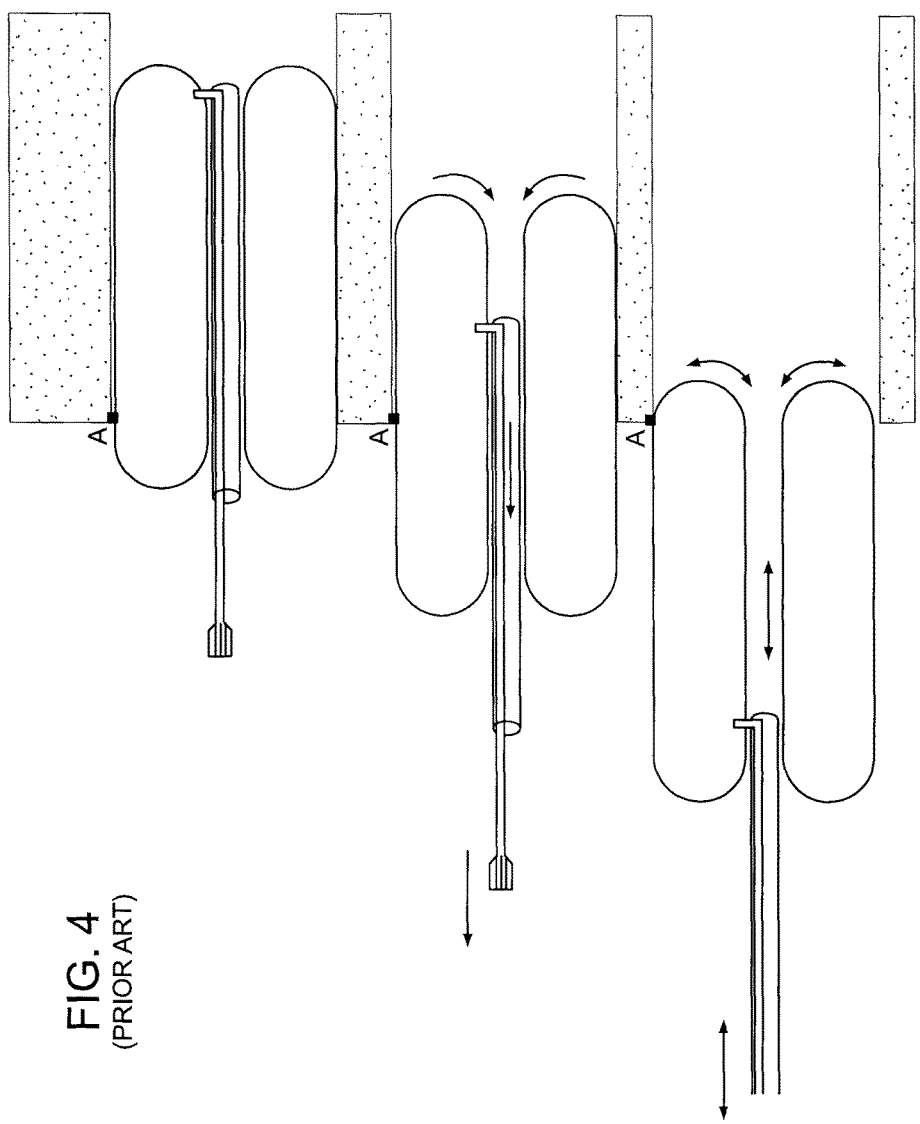
FIG. 4 depicts a series of diagrams that demonstrate the rotation of a toroidal balloon constructed over a tube where both tube and inflation port are attached at the same site on the toroidal balloon

The rotating toroidal balloon has at least the following unique and beneficial properties:
- To change location of the balloon, the balloon rotates or rolls over the surface.
- The walls of the balloon do not drag over the biological surface, minimizing trauma to the surface. The balloon is peeled off the biological surface. With rotation, the wall of the balloon is removed perpendicularly from the surface.
- The balloon can be constructed over a tube through its inner channel, creating a space within the balloon. FIG. 3 is a group of diagrams that explain subsequent diagram in this invention's art. This allows maintenance of the channel whether the balloon is dilated. The tube can allow positioning of the balloon over a guide or provide a free passage to allow fluid flow, gas flow or passage of instruments.
- The inflation port of the balloon can enter the toroidal balloon at any location on the balloon depending upon its function. In FIG. 4, the inflation port enters the balloon at the leading end of the balloon's inner channel and moves through the inner channel with rotation of the balloon. In FIG. 5, the inflation port enters the toroidal balloon on its external wall and does not move with internal rotation of the balloon.

Inflation of the balloon may permit a uniform pressure across the biological wall.

The toroidal balloon can have an asymmetric or irregular construction to fill and asymmetric or irregular space with inflation yet still retain its ability to rotate.

In addition, the toroidal balloon may be associated with at least the following accessories:

A device to measure pressure or release pressure. This controlled pressure may be set to apply adequate pressure to achieve the balloon's purpose while not too much pressure to damage or inhibit blood flow within the biological structure.

A lubricious coating.

A diaphragm closing the space in the balloon's inner channel but still allowing balloon rotation.

A biologically active substance such as a coagulant on the balloon's outer or inner surface that is applied to the opposing biological wall with balloon inflation.

A device such as coronary artery stent which is pushed into place with inflation of the balloon which is then left in place when the balloon is withdrawn through rotation.

In one embodiment, the toroidal balloon may be advanced into a target space in a deflated state and, then, inflated once in position. Removal is then performed in a partially or fully inflated state by rolling the balloon out through its internal channel with low friction. In this case, the external walls of the balloon remain in direct opposition to the biological structure and may apply pressure until taken down perpendicular to the surface with rotation of the balloon, while not dragging the balloon across the opposing biological structure.

In one embodiment, the present invention provides an apparatus comprising: a toroidal balloon comprising an internal balloon surface and an external balloon surface, the external balloon surface of the toroidal balloon configured for contacting and applying pressure against a biological wall, the balloon configured to rotate with low friction through inversion without sliding of the external surface against the biological wall and this inflated balloon configured to rotate into place or out of place and where the balloon is constructed of a material that allows low friction rotation and where the balloon is constructed with a material that is appropriate in composition and thickness for needed pressure, durability and biologic safety; an inflation port located on the balloon's surface where the location depends upon the intended function of the balloon; an implement which is attached to the balloon at one point that can be used to cause rotation of the balloon where the implement may be a catheter, an inflation port, a tube or other medical device.

In another embodiment, the present invention provides an apparatus comprising: a toroidal balloon comprising an internal balloon surface and an external balloon surface, the internal balloon surface of the toroidal balloon configured for contacting and applying pressure against a biological wall, the balloon configured to rotate through inversion without sliding of the internal surface against the biological wall and this inflated balloon configured to rotate into place or out of place with low friction and where the balloon is constructed of a material that allows low friction rotation and where the balloon is constructed with a material that is appropriate in composition and thickness for needed pressure, durability and biologic safety; an inflation port located on the balloon's surface where the location depends upon the intended function of the balloon; an implement which is attached to the balloon at one point that can be used to cause rotation of the balloon where the implement may be a catheter, an inflation port, a tube or other medical device.

The toroidal balloon may be used for tamponade, compression, dilation, expansion, placement of a biologically active substance or placement of a device from its external surface similar to a more traditional sausage-shaped or spherical balloon. An improvement over traditional sausage-shaped or spherical balloons, the toroidal balloon has two potential benefits: it can be constructed over a tube and it can be rolled into place or out of place without dragging the external balloon surface across the opposing biological wall. The rolling motion with balloon movement avoids the scraping or abrading of the biological surface. With toroid balloon motion, the external balloon surface is removed perpendicularly from the opposing surface rather than across the opposing surface. Toroidal balloon motion results in less pain and less trauma with removal compared with a simple sausage-shaped or spherical balloon.

There are multiple examples of insertion of a deflated toroidal balloon followed by inflation once in position and subsequently removal of the inflated balloon through internal rotation, some of which are described below.

Figure 6:
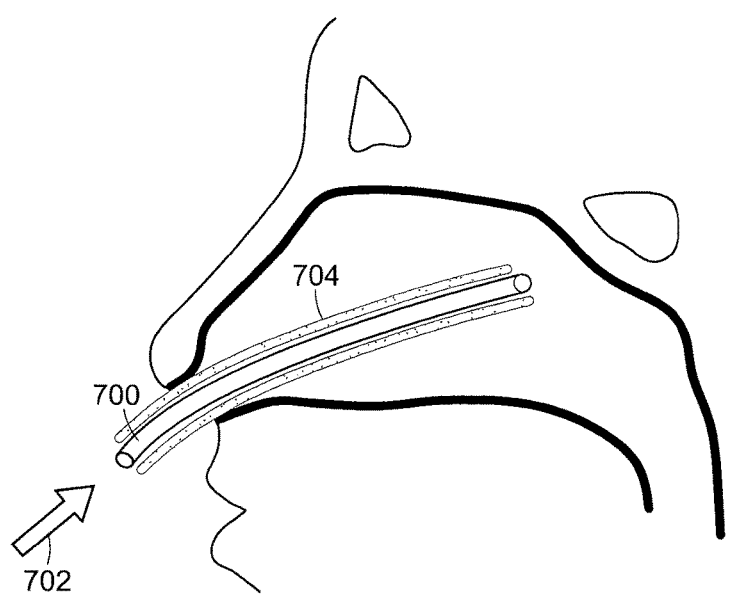
FIG. 6 depicts a diagram demonstrating the insertion of an un-inflated toroidal balloon constructed over a tube where the toroidal balloon is attached to the tube at its distal end.
Figure 7B:
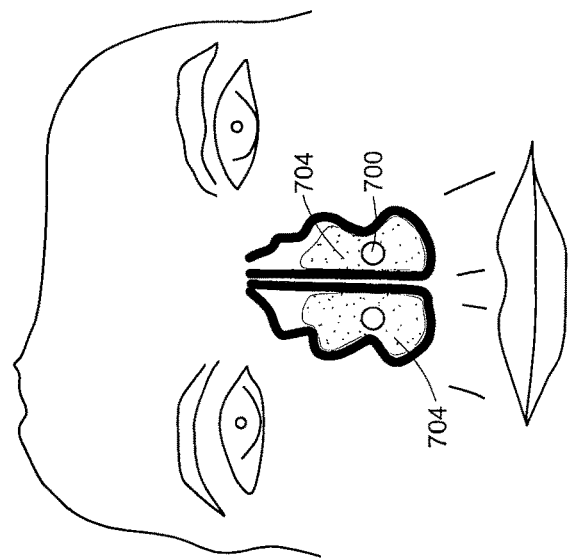
FIGS. 7A-7B depict diagrams demonstrating an inflated toroidal balloon constructed over a tube to allow passage of air and situated in the nasal cavities.
Figure 7A:
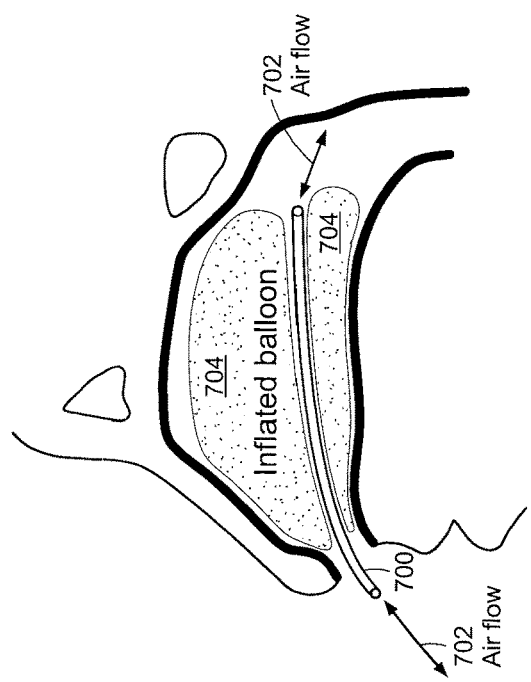
Figure 8:
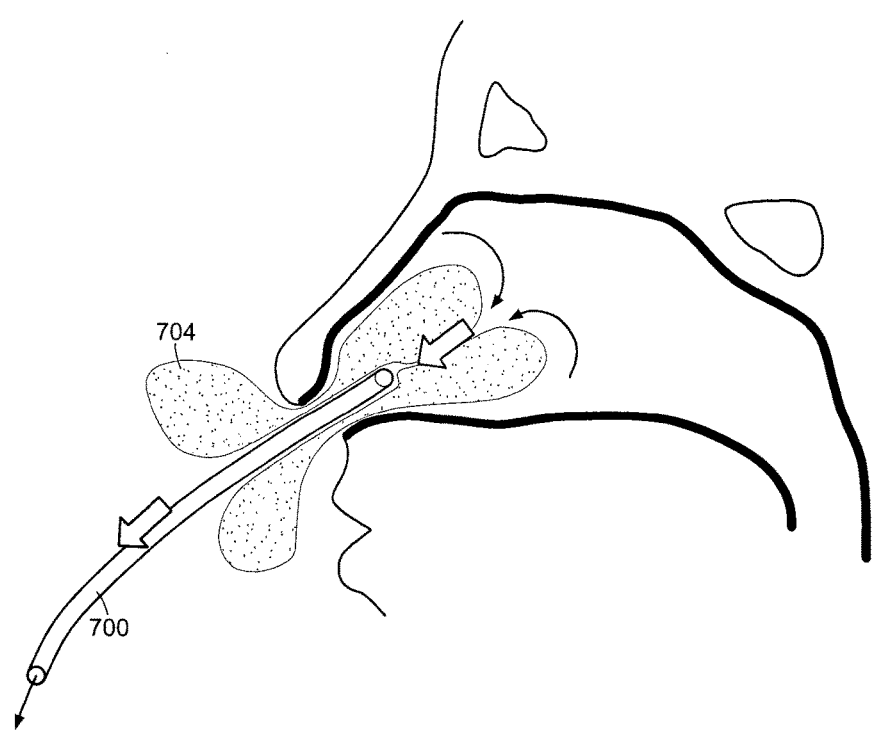
FIG. 8 depicts a diagram of the insertion of the rotational removal of an inflated toroidal balloon constructed over a tube where the external surface of the toroidal balloon remains stationary against the walls of the nasal cavity.

In another embodiment, the present invention provides a nasal splint. The nasal cavity is packed with gauze following repair of a deviated nasal septum. This packing provides hemostasis by applying direct pressure to the operative bed. In addition, the packing preserves and protects the passageway while the tissue heals after surgery. The subsequent removal of the packing, however, is painful and risks injury to the surgical repair site as the gauze drag across the delicate repair. Furthermore, the physical presence of the packing blocks airflow while in place. The use of a toroidal balloon 704 to apply pressure is an improvement over traditional packing. In this configuration, the balloon 704 is constructed over a tube 700 to allow airflow 702 through the balloon's inner channel. In this technique, as shown in FIG. 6, a toroidal balloon 704 is inserted into position on each side of the nasal septum in a deflated state. Once in position, the balloons 704 are then inflated, as depicted in FIGS. 7A and 7B. The pressure within the balloons 704 may be controlled in response to local anatomic and physiologic conditions and is determined by the medical clinician. For example, the clinician may elect a higher pressure for more brisk bleeding or a larger volume of inflation for a large capacity nasal cavity. The balloon is inflated through a standard syringe port per routine with existing epistaxis balloons. When the balloons 704 are no longer required for tamponade and support of repaired structures while healing, the tube 700 running though the toroid's inner channel is pulled from the nasal cavity causing rotation of the balloon and resulting in removal of the balloon with minimal pain and tissue trauma (FIG. 8).

In this embodiment, the present invention provides a nasal splint comprising: (A) a first tube and a first toroidal balloon constructed over at least a portion of the first tube, a first internal balloon surface of the first toroidal balloon contacting outside of the first tube and a first external balloon surface of the first toroidal balloon contacting tissue in a first nasal cavity to the left of a nasal septum, the first toroidal balloon deployed in the first nasal cavity in a deflated or partially inflated state; (B) a second tube and a second toroidal balloon constructed over at least a portion of the second tube, a second internal balloon surface of the second toroidal balloon contacting outside of the second tube and a second external balloon surface of the second toroidal balloon contacting tissue in a second nasal cavity to the right of the nasal septum, the second toroidal balloon deployed in the second nasal cavity in a deflated or partially inflated state; and (C) a pressure means to inflate the first and second toroidal balloon to apply a predetermined amount of pressure (picked, for example, to avoid pressure points and local ischemia) in the left and right nasal cavities. In an extended embodiment, upon completion of a procedure associated with the nasal splint, the pressure means partially deflates the first and second toroidal balloon, where the first and second toroidal balloon are each removed via an inversion of their corresponding internal balloon surface and external balloon surface, with such inversion allowing low friction extraction of the first and second toroidal balloons without sliding of the external balloon surfaces against wall tissue in the first and second nasal cavities. In an extended embodiment, the first and second toroidal balloons are in the partially inflated state when deployed in the first and second nasal cavities, respectively, with the deployment being done via an inversion of their corresponding internal balloon surface and external balloon surface, with such inversion allowing low friction placement of the first and second toroidal balloons in the first and second nasal cavities without sliding of the external balloon surfaces against wall tissue in the first and second nasal cavities.

In another embodiment, the present invention provides for a tamponade balloon for epistaxis (nosebleeding). Existing tamponade balloons for epistaxis are simple balloons which, when inflated, apply direct pressure to a bleeding surface. Such devices expand radially and do not allow airflow while inflated. There exist nasal balloons constructed over a tube to allow airflow, however, these existing balloons are not toroidal balloons that allow atraumatic removal with rotational extraction. To remove the existing balloon, it is deflated then withdrawn which risks scraping of the fresh clot and re-bleeding. A toroidal balloon constructed over a tube allows external direct pressure while permitting the flow of air with respiration and minimal disruption of the fresh clot but removal with toroidal balloon rotation. The toroidal balloon need not be of symmetric construction as in the case of existing spherical or sausage-shaped balloon and can be made to approximate the inner anatomic cavity of the nasal passage yet still be moved with internal rotation of the balloon (FIGS. 7A and 7B). By better approximating the nasal cavity when inflated, the pressure within the flexible balloon is more uniform across a larger area on the balloon's external surface, avoiding pressure points and localized ischemia.

In this embodiment, the present invention provides a tamponade device for epistaxis comprising: (A) a tube and a toroidal balloon constructed over at least a portion of the tube, an internal balloon surface of the toroidal balloon contacting outside of the tube and an external balloon surface of the toroidal balloon contacting tissue in a nasal cavity which is the site of the epistaxis, the toroidal balloon deployed in the nasal cavity in a deflated or partially inflated state; and (B) a pressure means to inflate the toroidal balloon to apply a predetermined amount of pressure (picked, for example, to avoid pressure points and local ischemia) to the site of epistaxis. In an extended embodiment, upon completion of a procedure associated with the tamponade device (e.g., successful clotting at the site of epistaxis), the pressure means partially deflates the toroidal balloon, with the toroidal balloon removed via an inversion of its internal balloon surface and external balloon surface, with such inversion allowing low friction extraction of the toroidal balloon without sliding of the external balloon surfaces against wall tissue in the site of epistaxis. In an extended embodiment, the toroidal balloon is in the partially inflated state when deployed in the site of epistaxis, and the deployment done via an inversion of the internal balloon surface and the external balloon surface, with such inversion allowing low friction placement of the toroidal balloon in the site of epistaxis without sliding of the external balloon surfaces against wall tissue in the site of epistaxis. In an extended embodiment, the internal and external balloon surfaces are coated with a coagulogenic substance. In an extended embodiment, the epistaxis catheter is constructed with both a toroidal balloon as above and also a simple balloon at a separate site along tube 700 to apply focal pressure as in the case of existing toroidal balloons.

Figure 10:
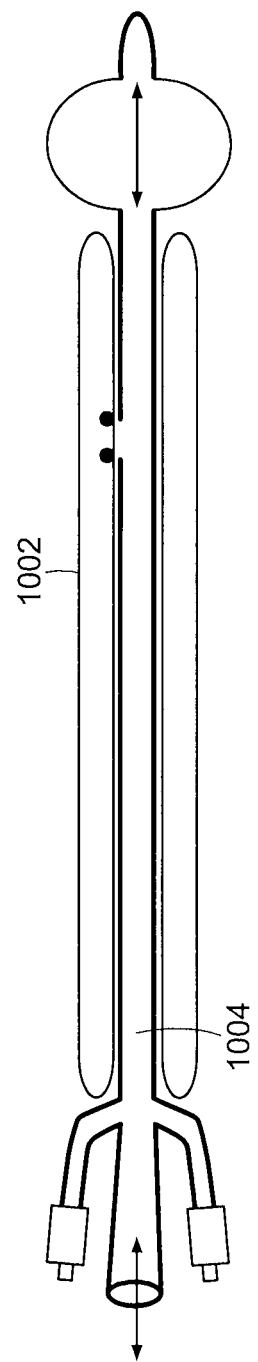
FIG. 10 depicts another example of a toroidal balloon constructed over a urethral catheter where both tube and inflation port are attached at the same site on the toroidal balloon. In this case, the toroidal balloon is left inflated while in-situ, creating a low friction layer between the catheter and the urethra to minimize painful tugging on the urethra.

The present invention, in another embodiment, provides a urethral catheter for painless extraction and wear. A major source of anxiety and discomfort for patients with indwelling urethral catheters, such as Foley catheters, is the extraction of the catheter when no longer required for medical purposes. With removal of the catheter, the often redundant and deflated balloon and the catheter wall are dragged across the sensitive urethral wall. The discomfort can be worse with a more long-term indwelling Foley where the urethra can become inflamed and ulcerated. A novel urethral catheter equipped with a toroidal balloon is uniquely and ideally suited to decrease the pain and discomfort associated with extraction of the catheter. The technique involves insertion of a urethral catheter whose length is covered by an uninflated toroidal balloon 904, as depicted in FIG. 9A. Before extraction of the balloon, the retention balloon 902 is deflated per routine. The toroidal balloon 904 is then inflated and the catheter is pulled out causing rotation of the toroidal balloon 904, as depicted in FIG. 9B. Since the outside wall of the balloon remains stationary against the urethral wall and the catheter is removed through the toroidal balloon's inner channel 906, there is no friction and catheter extraction is painless, as depicted in FIG. 9C. Of note, a urethral catheter equipped with a toroidal balloon may also be more comfortable while indwelling. If the balloon is partially inflated while in situ, the catheter will freely slide in and out with patient activity since there is little friction between the balloon layers. The catheter wall does not drag across the sensitive urethral wall because of the slippery layer, as depicted in FIG. 10.

In this embodiment, the present invention provides a urethral catheter comprising: (A) a tube having a retention balloon at distal end; (B) a toroidal balloon constructed over a portion of the tube, an internal balloon surface of the toroidal balloon contacting outside of the tube and an external balloon surface of the toroidal balloon contacting a urethral wall, the toroidal balloon deployed in the urethra in a deflated or partially inflated state and not covering the retention balloon; and (C) a first pressure means to inflate the retention balloon when deployed in the urethra and deflate the same when a urethral procedure is complete; (D) a second pressure means to inflate the toroidal balloon, with the deflated retention balloon extracted via an inversion of the toroidal balloon's internal balloon surface and external balloon surface, with such inversion allowing low friction extraction of the retention balloon without sliding of the external balloon surfaces against the urethral wall. In an extended embodiment, the toroidal balloon is at least in a partially inflated state when deployed in the urethra, and the retention balloon is deployed in a deflated state in the urethra via an inversion of the toroidal balloon's internal balloon surface and external balloon surface, with such inversion allowing low friction placement of the retention balloon without sliding of the external balloon surfaces against the urethral wall. In an extended embodiment, the internal and external balloon surfaces are coated with a coagulogenic or antimicrobial substance. In an extended embodiment, the first and second pressure means are the same.

In another embodiment, the present invention provides a urethral catheter for tamponade of urethral bleeding. A vexing problem without an active solution at present is the treatment of urethral bleeding. The urethral is surrounded by a highly vascular structure called the corpus spongiosum. Injury of this delicate structure as in the case of a misplaced urethral catheter results in severe hemorrhage. It is conceivable that insertion of a deflated toroidal balloon 1002 coated with a coagulogenic substance and constructed over a tube 1004 such as a Foley catheter, followed by inflation of the tube can cause tamponade of the bleeding urethral injury and application of the coagulogenic factor. Once the bleeding has ceased and clot has formed, the tamponade balloon 1002 is extracted through toroidal rotation which leaves the coagulogenic substance in place and minimizes disruption of the new clot. The urethral catheter for this purpose is also demonstrated in FIG. 10.

In this embodiment, the present invention provides a urethral catheter for tamponade of urethral bleeding comprising: (a) a tube having a retention balloon at distal end; (b) a toroidal balloon constructed over a portion of the tube, an internal balloon surface of the toroidal balloon contacting outside of the tube and an external balloon surface of the toroidal balloon contacting a urethral wall, the toroidal balloon deployed in the urethra in a deflated or partially inflated state and not covering the retention balloon, the internal and external balloon surfaces coated with a coagulogenic substance; (c) a first pressure means to inflate the retention balloon when deployed in a site of urethral bleeding in the urethra and deflate the same when a urethral procedure is complete; and (d) a second pressure means to inflate the toroidal balloon when deployed in the site of urethral bleeding, where the inflated toroidal balloon coated with the coagulogenic substance contacts a urethral wall that is the site of urethral bleeding. In an extended embodiment, where, when the urethral bleeding is contained, the deflated retention balloon extracted via an inversion of the toroidal balloon's internal balloon surface and external balloon surface, with such inversion allowing low friction extraction of the retention balloon without sliding of the external balloon surfaces against the urethral wall. In an extended embodiment, the toroidal balloon is in a partially inflated state when deployed in the urethra, and the retention balloon is deployed in a deflated state in the urethra via an inversion of the toroidal balloon's internal balloon surface and external balloon surface, with such inversion allowing low friction placement of the retention balloon without sliding of the external balloon surfaces against the urethral wall. In an extended embodiment, the first and second pressure means are the same.

Figures 5A, 5B, 5C:
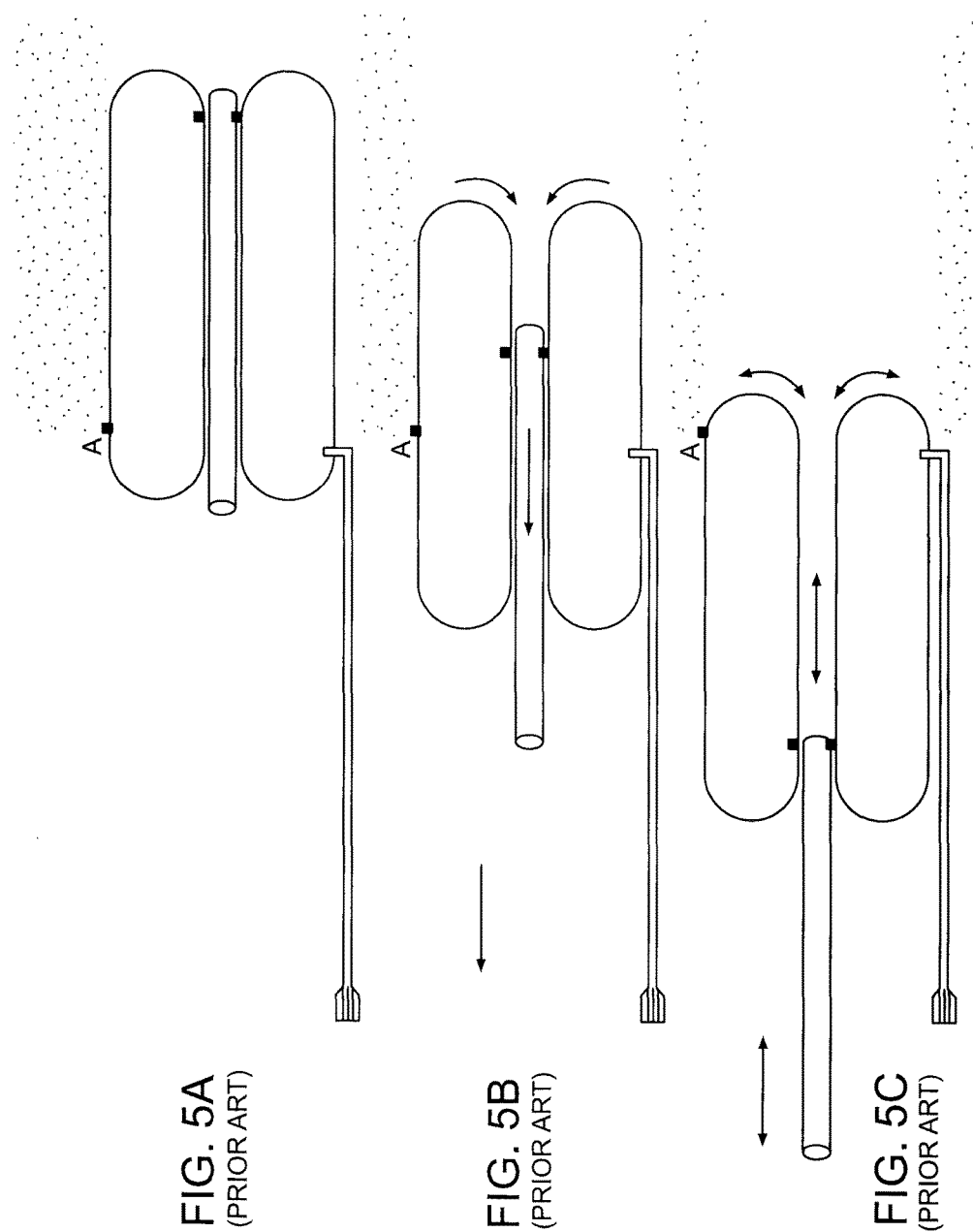
FIGS. 5A-5C depict a series of diagrams that demonstrate the rotation of a toroidal balloon constructed over a tube where the tube and inflation port are attached at separate sites on the toroidal balloon.

In the various embodiments described above, the toroidal balloon may be rolled into a space in an inflated state (or partially inflated state) by low friction internal rotation of the balloon as depicted in FIG. 5C. This allows the changing of the balloon's position without dragging the outside walls against the biological wall. The balloon is then removed in either a deflated state without rotation or a partially of fully inflated state with rotation.

In the various embodiments described above, the toroidal balloon may be advanced into place over an object through the internal channel in a deflated state such as over a glide wire. This allows guidance of the deflated toroidal balloon into place with the inner channel surrounding the guide. The balloon is inflated which then applies pressure along the balloon's inner channel so that the surface of the inner channel does not slide against the object within the inner channel with rotation of the toroidal balloon.

In the various embodiments described above, the toroidal balloon may be advanced into place over an object or biological structure in an inflated state by rolling the balloon over the object. This allows changing the balloon's position without dragging the internal balloon surface across the biological object within the balloon's inner channel.

Figure 11:
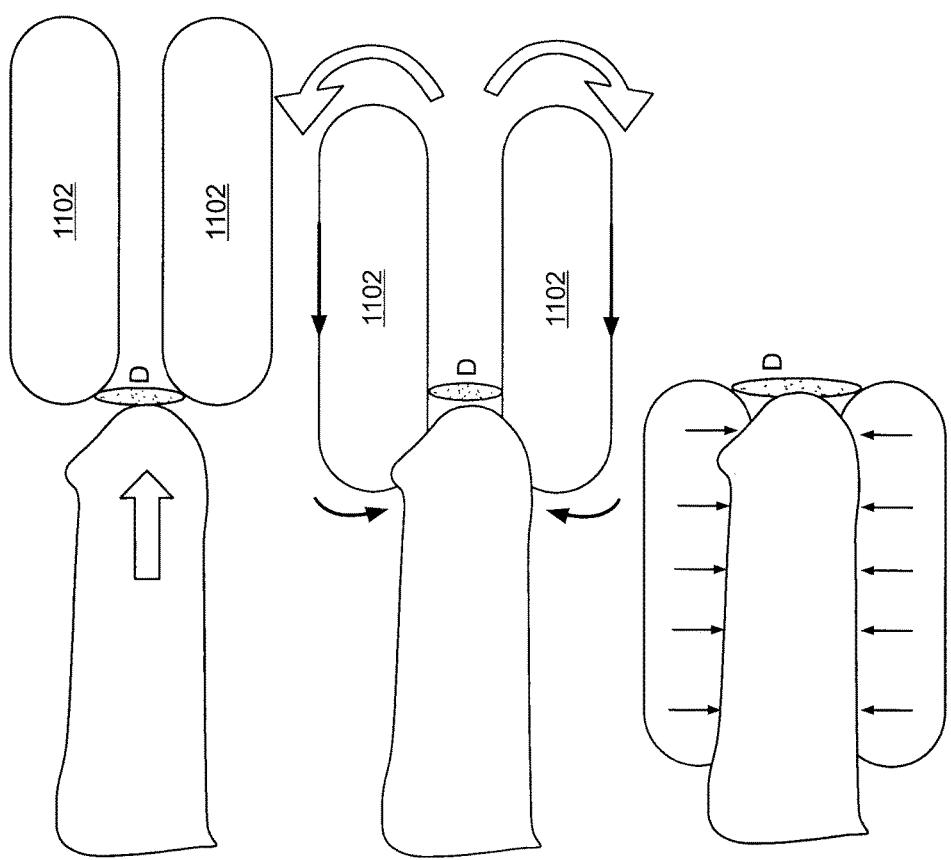
FIG. 11 depicts an example of a device for male urinary incontinence where the toroidal balloon is rolled onto place while inflated exerting uniform pressure along its inner channel. The part labeled "D" represents a diaphragm that occludes the inner channel of the balloon.

A non-limiting example of an inflated toroidal balloon 1102 rolled into place to apply external pressure to a biological structure is a device for male urinary incontinence as depicted in FIG. 11. In this example device, a specially designed toroidal balloon 1102 with a diaphragm D is rolled over the penis to apply a controlled and evenly distributed pressure over the urethra. The pressure can be set to squeeze the penis enough to disallow passage of urine through the urethra while allowing blood flow to the tissues. The pressure on the penis from the balloon's internal channel will hold the incontinence device onto the penis and form a seal where trapped urine under the diaphragm cannot escape. Of practical note, in this example, an attachment may be necessary to keep the balloon from rolling back off the penis once situated.

Figure 12:
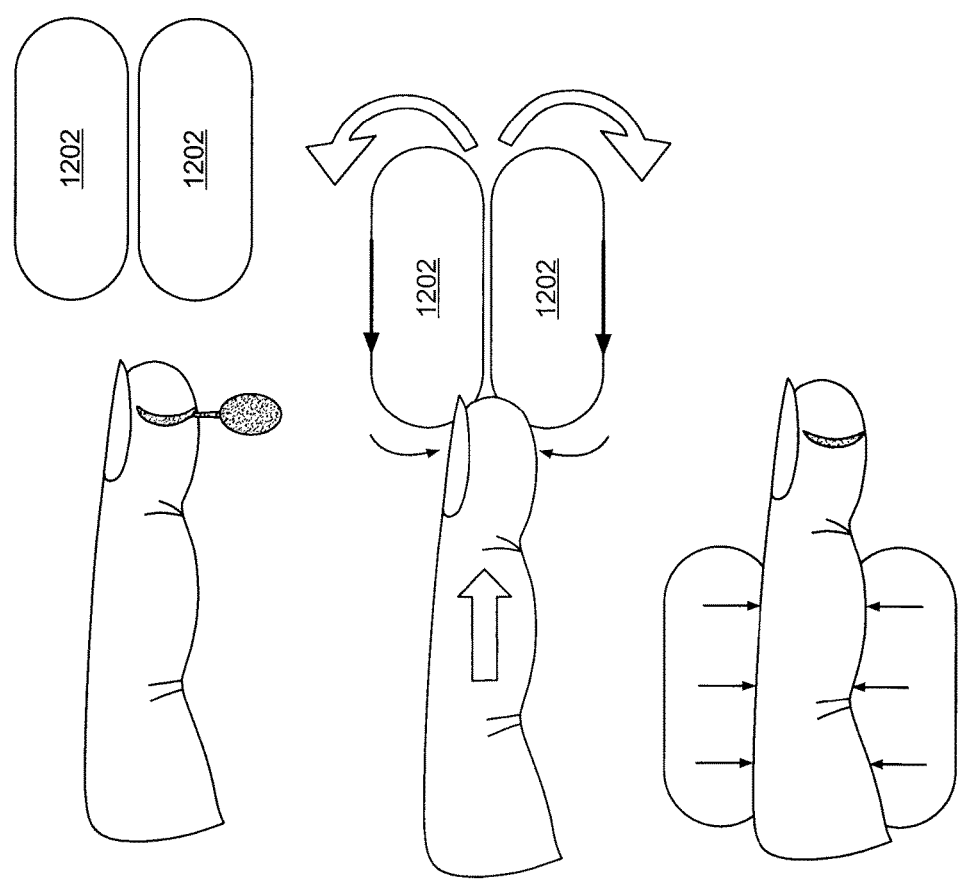
FIG. 12 depicts an example of a toroidal balloon used as a tourniquet to repair a finger laceration where the toroidal balloon is rolled onto place while inflated under high pressure exerting uniform pressure along its inner channel.

Another non-limiting example of a device using the rolling into place of a toroidal balloon 1202 in an inflated state for the exertion of pressure over an object via its inner wall is a novel tourniquet, as depicted in FIG. 12. Similar to the balloon in FIG. 11, but under greater balloon pressure to disallow blood flow. In addition, the rolling into place of the toroidal balloon 1202 tourniquet squeezes blood out of the finger with placement for a bloodless operative field.

CONCLUSION

A system and method has been shown in the above embodiments for the effective implementation of a toroidal balloon for external or internal compression with unique insertion or removal. While various preferred embodiments have been shown and described, it will be understood that there is no intent to limit the invention by such disclosure, but rather, it is intended to cover all modifications and alternate constructions falling within the spirit and scope of the invention, as defined in the appended claims. For example, the present invention should not be limited by size, materials, or specific manufacturing techniques.

The invention claimed is:
1. A urethral catheter comprising:
a tube having a retention balloon at distal end;
a toroidal balloon constructed over a portion of the tube, an internal balloon surface of the toroidal balloon contacting outside of the tube and an external balloon surface of the toroidal balloon configured to contact an urethral wall, the toroidal balloon configured to be deployable in the urethra in a deflated or partially inflated state and not covering the retention balloon; and
a first pressure means to inflate the retention balloon when deployed in a bladder and to deflate the retention balloon upon completion of a urethral procedure;
a second pressure means attached to the tube to inflate the toroidal balloon, the deflated retention balloon extractable via an inversion of the toroidal balloon's internal balloon surface and external balloon surface, with such inversion allowing low friction extraction of the retention balloon without sliding of the external balloon surfaces when contacting the urethral wall.

2. The urethral catheter of claim 1, wherein the toroidal balloon is at least in a partially inflated state when configured to be deployed in the urethra, and the retention balloon is configured to be deployed in a deflated state in the urethra via an inversion of the toroidal balloon's internal balloon surface and external balloon surface, with such inversion allowing low friction placement of the retention balloon without sliding of the external balloon surfaces when contacting the urethral wall.

3. The urethral catheter of claim 1, wherein the internal and/or external balloon surfaces are coated with any of the following, or combinations thereof: a coagulogenic substance or an antimicrobial agent.

4. The urethral catheter of claim 1, wherein the first and second pressure means are the same.

5. A urethral catheter for tamponade of urethral bleeding comprising:
  a tube having a proximal and distal end, the distal end having a retention balloon;
  a toroidal balloon constructed over a portion of the tube, an internal balloon surface of the toroidal balloon contacting outside of the tube and an external balloon surface of the toroidal balloon configured to contact a urethral wall, the toroidal balloon configured to be deployed in the urethra in a deflated or partially inflated state and not covering the retention balloon, the internal and external balloon surfaces coated with a coagulogenic substance; and
  a first pressure means to inflate the retention balloon when deployed in a bladder and configured to deflate the retention balloon when a urethral procedure is complete; and
  a second pressure means attached to the tube to inflate the toroidal balloon when deployed in the site of urethral bleeding, where the inflated toroidal balloon coated with the coagulogenic substance contacting the urethral wall that is the site of urethral bleeding.

6. The urethral catheter for tamponade of urethral bleeding of claim 5, where, when the urethral bleeding is contained, the deflated retention balloon extracted via an inversion of the toroidal balloon's internal balloon surface and external balloon surface, with such inversion allowing low friction extraction of the retention balloon without sliding of the external balloon surfaces when contacting the urethral wall.

7. The urethral catheter of claim 5, wherein the toroidal balloon is in a partially inflated state when configured to be deployed in the urethra, and the retention balloon is deployed in a deflated state in the urethra via an inversion of the toroidal balloon's internal balloon surface and external balloon surface, with such inversion allowing low friction placement of the retention balloon without sliding of the external balloon surfaces when contacting the urethral wall.

8. The urethral catheter of claim 5, wherein the first and second pressure means are the same.

* * * * *